Figure 1:
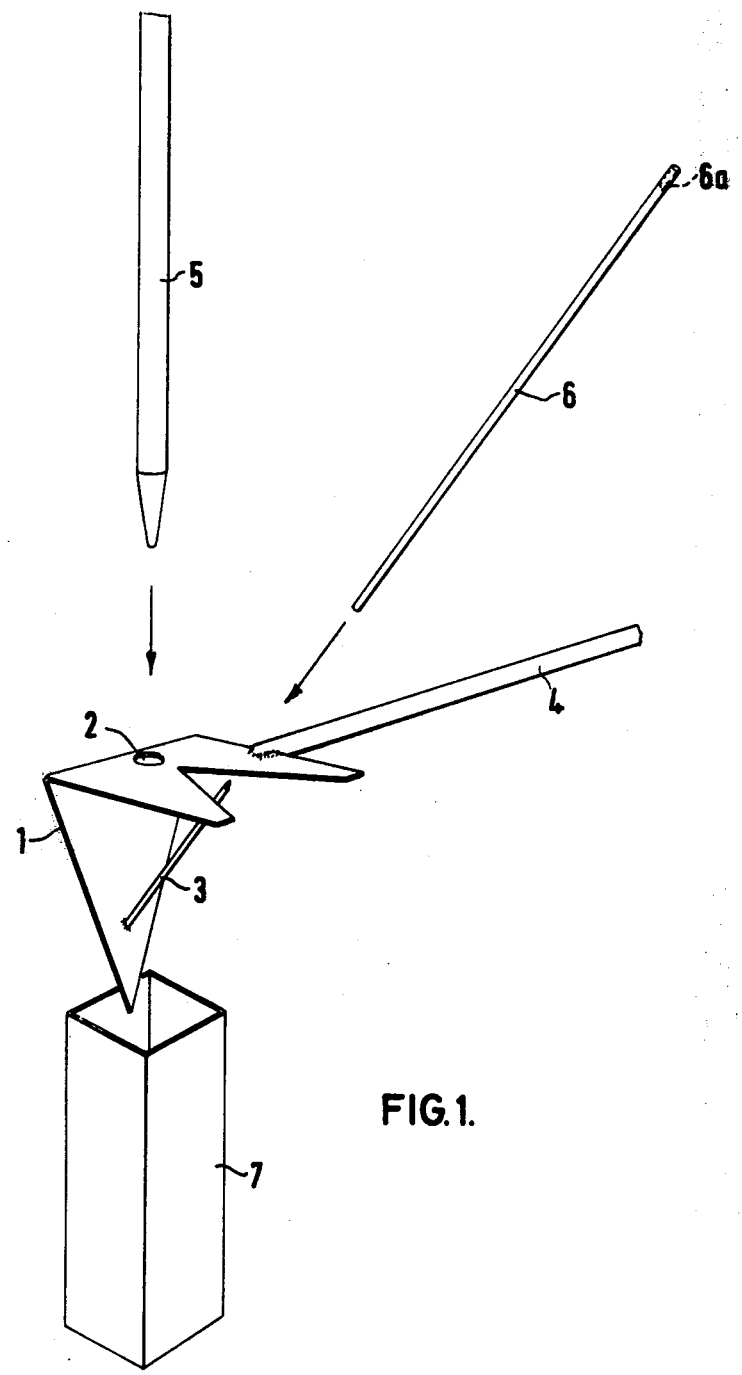

United States Patent [19]

Renshaw

[11] 4,152,939
[45] May 8, 1979

[54] MICRO-SAMPLING DEVICE

[76] Inventor: Alan Renshaw, Clinical Research Centre, Division of Clinical Chemistry, Watford Rd., Harrow, Middlesex HA1. 3UJ, England

[21] Appl. No.: 764,537

[22] Filed: Feb. 1, 1977

[30] Foreign Application Priority Data

Feb. 2, 1976 [GB] United Kingdom ............... 4072/76

[51] Int. Cl.² ............................................. G01N 1/10
[52] U.S. Cl. .......................... 73/425.4 R; 73/425.4 P
[58] Field of Search ................. 73/425.4 R, 425.4 P, 73/421 R; 128/28, DIG. 5, 218 C; 23/259; 222/148, 420

[56] References Cited

U.S. PATENT DOCUMENTS

| Re. 27,645 | 5/1973 | Drummond et al. | 128/218 C |
|---|---|---|---|
| 2,643,801 | 6/1953 | Kollmeyer | 222/420 |
| 2,943,624 | 7/1960 | Alquist | 128/218 C |
| 2,981,522 | 4/1961 | Spragens | 222/420 X |
| 2,989,215 | 6/1961 | Willingham | 222/420 X |
| 3,153,345 | 10/1964 | Berg | 73/423 R |
| 3,355,950 | 12/1967 | Harris, Sr. | 73/425.4 P X |
| 3,677,447 | 7/1972 | Rentz | 222/420 X |
| 3,992,150 | 11/1976 | Retzer | 73/425.4 P |
| 4,003,260 | 1/1977 | Cafoul | 73/425.4 R |
| 4,024,857 | 5/1977 | Blecher et al. | 128/2 F |

*Primary Examiner*—Daniel M. Yasich
*Attorney, Agent, or Firm*—Murray and Whisenhunt

[57] ABSTRACT

A device for obtaining a micro-sample of a liquid specimen, and includes a specimen container with a longitudinal capillary bore and a solid probe on a support which may be inserted totally or partially into the capillary bore to displace a micro-sample of known volume from the bore of the container. The device may be used for any liquid specimen for which micro-samples are required such as blood plasma.

10 Claims, 3 Drawing Figures

MICRO-SAMPLING DEVICE

This invention relates to a micro-sampling device and to a process for obtaining micro-samples of a liquid.

Much interest has recently been shown in the design of apparatus and techniques suitable for use in micro-sampling where adequate skills and facilities are not widely available. In particular, a micro-sampling technique is required for use in sampling blood for analysis. The micro-sampling device described herein is part of a development aimed at providing a simple and inexpensive system whereby a number of clinically significant tests may be performed by semi-skilled personnel on blood specimens.

The easiest method of obtaining a patient's blood specimen is by pricking a finger or ear lobe and allowing a small bore glass specimen tube to fill by capillary action. This method unfortunately yields only a small specimen volume, but two specimen tubes of 1 mm bore and 75 mm in length are normally filled with ease, thus giving two separate whole blood specimens of about 60 microliters each. Many clinical analyses are, however, performed on blood plasma, which necessitates separation of the red cells from the plasma. This separation is usually effected by a process of centrifugation which results in a further reduction of the volume of the test material. Eventually, about 15 microliters only may be available for analysis in each specimen capillary. Normally, an analysis of such a small volume using traditional methods requires skill, and accurately calibrated apparatus. The device of this invention is intended to offer an appropriate alternative to traditional techniques.

The device of this invention is one for obtaining a micro-sample of a liquid and comprises a specimen container having a longitudinal capillary bore and a probe adapted for insertion into the capillary bore, the probe or a part thereof being of a volume equal to the desired volume of the micro-sample so that insertion of the probe or a part thereof into a container having a specimen in the bore thereof displaces from the bore a micro-sample of the desired volume.

When only a part of the probe is to be inserted, means for indicating the length of the probe to be inserted are provided. Preferably, the probe is of a volume equal to the desired volume of the micro-sample. To the sample so obtained by displacement may then be added a suitable diluent when it is required to analyse the sample. The diluent may be added, for example, by means of a pipette so positioned as to wash the liquid sample displaced down into a reaction vessel or colorimeter cuvette or the diluent may already be measured into the reaction vessel and the measured sample stirred into it. After addition of a suitable reagent required in the analysis of the liquid of after suitable incubation, readings may be taken in the usual manner using conventional devices such as a flame photometer, colorimeter or absorptiometer or radioactive counting.

It will be appreciated that for the device of this invention to operate, the diameter of the bore of the specimen container and the shape of the probe must be such as to permit the release of liquid from the bore of the specimen container containing a specimen on inserting the probe. Also, of course, the shape of the probe and the bore in the capillary should be such that a seal due to surface tension is maintained between the probe and the walls of the bore when the probe is in the bore so that when the displaced fluid is washed off no further sample is extracted thereby from the bore.

According to one embodiment of the invention, the probe may be provided in the form of a probe unit which comprises: a solid, elongate, typically substantially cylindrical, member and a member having two planar portions connected to one another substantially at right angles, the solid elongate member being attached at an acute angle to one of said planar portions in the direction of said other planar portion such that the free end of the solid elongate member is positioned in relation to said other portion so as to enable the solid, elongate member to be inserted into the bore of the specimen container, the portion to which the solid elongate member is attached terminating in a vertex. Advantageously, the planar portion to which the solid elongate member is not attached is provided with a hole adjacent to the angle between the two planar portions through which a pipette containing diluent may be inserted in order to wash the displaced micro-sample down into a reaction vessel.

According to a further embodiment of the invention the probe may be provided in the form of a probe unit which comprises a platform to one, preferably dished, face of which is attached (a) a solid elongate, typically substantially cylindrical member and (b) a support rod which is substantially parallel to (a).

According to a still further embodiment of the invention the probe may be provided in the form of a probe unit which comprises: a solid elongate, typically substantially cylindrical, member and connected thereto a support rod held substantially parallel and in the same sense, to said elongate member; a rod-shaped member having at least one transverse notch along its length and being adapted at one end for holding the specimen container axially thereto; and a device attached to the support rod adapted to engage the at least one notch in the rod-shaped member, said device being slidably mounted on said rod-shaped member.

The probe units per se as defined above also form part of this invention.

The present invention also provides a process for obtaining a micro-sample of a liquid, wherein a probe or a part thereof equal in volume to the micro-sample required is inserted into the longitudinal capillary bore of a container containing a specimen of the liquid so as to displace from the bore a micro-sample of the desired volume. Means are provided for indicating the length of the probe to be inserted when only partial insertion is required.

Although this invention is being described with reference to the sampling of blood for analysis, it is to be understood that it may be used to sample other liquids for which small samples are required, such as for reagents and diluents for use in analyses.

Figure 2:
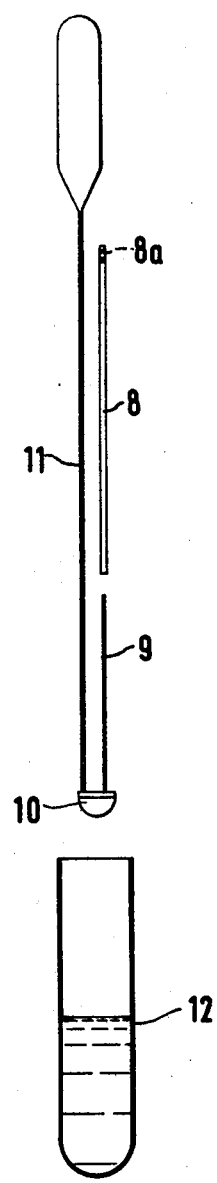
Figure 3:
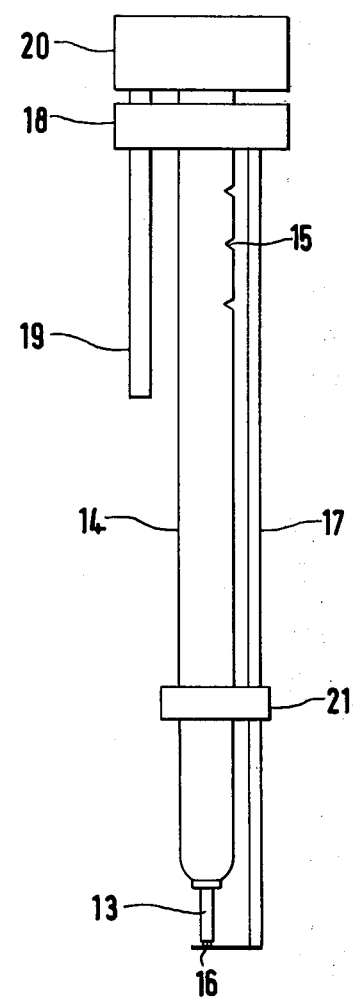

Illustrative embodiments of the invention will now be described by way of example with reference to the accompanying drawings in which:

FIG. 1 is a diagrammatic perspective view of a micro-sampling device according to one embodiment of this invention, FIG. 2 is a schematic representation of a micro-sampling device according to another embodiment of this invention, and FIG. 3 is a schematic representation of a micro-sampling device according to a further embodiment of this invention.

Referring initially to FIG. 1, this illustrates one embodiment of the invention which comprises a piece of sheet 0.5 mm thick, cut and bent into the shape shown, the width of this fabrication (1) being about 20 mm at its widest point. This sheet may be of a stainless steel or another material, for example polytetrafluoroethylene or nylon which is not corroded by or does not otherwise react with the liquids used in the analysis. A hole of approximately 3 mm diameter (2) is provided in order to receive the tip of a pipette which adds the diluent. A probe (3) is secured, for example, hard soldered in position as shown. This probe may be for example of stainless steel wire (e.g. 20 S.W.G. 0.94 mm diameter) and may or may not be of the same material as the fabrication (1), although similar considerations as to the material used apply. The probe (3) projects at about 45°, and terminates within the V cut in the fabrication (1). The volume of the probe (3) must be exactly equal to the required volume of the sample because the device operates by displacement. The probe (3) is therefore cut so that its volume is 10 cu mm, 15 cu mm, and 20 cu mm, when samples of 10 μl, 15 μl and 20 μl respectively are required. A stainless steel rod (4) serves as a support. A specimen capillary (6) plugged at its upper end by a plug (6a), is positioned so that it can be threaded over the probe (3) until the open end of the capillary tube (6) contacts fabrication (1) to release the desired volume of sample. The lower end of the stainless steel fabrication (1) terminates in a "V" which is placed inside the mouth of a colorimeter cuvette (7). This ensures that all of the sample released by the probe (3) and also the diluent added by means of the pipette (5) is directed inside the colorimeter cuvette (7). Any of the sample which remains adhered to the fabrication (1) is washed into the cuvette by the diluent added through hole (2) from the pipette (5).

FIG. 2 illustrates a further embodiment of the invention which may offer advantages over the type of device illustrated in FIG. 1. This device comprises a capillary tube (8), plugged at its upper end by a plug (8a), a probe (9) attached at its lower end to a platform (10), which suitably is circular and may be dished, supported by a support rod (11), and a tube or cuvette (12) into which a diluent has previously been measured. In operation, the probe (9) is threaded into the capillary tube (8) until the open end of the capillary tube (8) contacts platform (10) and the platform (10), still supporting the capillary, becomes wetted with the sample. The platform (10) is then lowered into the tube or cuvette (12) containing the diluent and stirred in by gentle movement so that all of the measured sample is mixed into the diluent. The probe (9), platform (10) and support rod (11) may each be fabricated of stainless steel or another material which is not corroded by, or does not otherwise react with, the sample, reagent and diluent.

FIG. 3 illustrates a further embodiment of the invention, comprising a capillary tube (13) mounted in a holder (14) which has notches or "click stops" (15) in its upper portion. A probe (16), shown here fully inserted in the capillary tube (13), is attached via a support rod (17) to a moveable actuator (18). An actuator guide (19) is provided attached to the top (20) of the holder (14) and passing through the moveable actuator (18) and a support rod guide (21) for the support rod (17) is provided on the holder (14).

In operation, the capillary tube (13) containing the liquid is mounted in the holder (14) and the probe (16) is aligned by means of actuator guide (19) and support rod guide (21) with the probe (16) not inserted in the capillary tube (13). The actuator (18) engages with the notches (15) which are placed at intervals, and act as the controlling means for controlling the extent of insertion of the probe, such that by raising the actuator (18) through one or more of these intervals the probe (16) enters the capillary tube (13) to displace a measured amount of the liquid.

Such a device can be used for displacing a specific volume but also can be used where the same probe is required to displace different sample volumes. For example, the notches may be at positions representing 5 μl, 10 μl, 15 μl and 20 μl, so that, by raising the actuator (18) past the appropriate number of notches, samples of any of these volumes may be obtained.

The micro-sampling device according to the embodiment illustrated in FIG. 1 may be used in the following manner for analysing a blood sample:

A finger is pricked, and a volume of blood is allowed to form. If the finger is held horizontally, sufficient blood adheres to the finger to continuously fill a heparinized specimen capillary (6) of 1 mm bore × 75 mm in length, also held horizontally. One end of the specimen capillary, is plugged by a plug (6a), for example with a small amount of a pliable material such as a wax, or modelling clay, or by otherwise sealing the tube end. A second specimen is taken in a similar way, and the specimens are placed in a centrifuge, and spun for 4–5 minutes. A simple two-place centrifuge may be employed which utilises an inexpensive 12 v D.C. motor. Adequate separation of plasma can be achieved in 4–5 minutes, using only 6 watts of electric energy. One specimen capillary is then taken, and after noting that the now separated plasma fraction fully reaches the unplugged end of the specimen capillary, the open end of the capillary is fully threaded onto the probe (3) of the micro-sampling device and remains so threaded throughout the operation. (If a small air bubble is observed at the open end of the specimen capillary, another small amount of wax or other plugging material may be pressed into the plugged end before the probe is inserted and any serum overflow is wiped away). The pipette (5) is filled with a suitable volume of reagent, the tip of the pipette is inserted into the hole (2) provided in the fabrication (1), and is allowed to discharge. In so doing, the collected drop of serum displaced by the probe is washed down into a colorimeter cuvette, or reaction vessel (7). The lower end of the stainless steel fabrication terminates in a "V" which enters the mouth of the recipient vessel, ensuring all the sample and reagent is directed inside the vessel.

The other sample capillary is then treated in a similar way. After a period of incubation, or the addition of another reagent, depending upon the analysis being performed, the results for each sample obtained are measured in an Absorptiometer in the traditional way thus providing a duplicate set of results of the analysis.

The micro-sampling device according to the embodiment illustrated in FIG. 2 may be used in the following manner to analyse a blood sample:

Two specimen capillaries are filled, centrifuged and sealed at one end as described hereinabove and the required amount of diluent is measured in a vessel or cuvette (12). One specimen capillary tube (8) is then taken and after noting that the separated blood plasma reaches the unplugged end of the specimen capillary, the open end of the capillary is fully threaded onto the probe (9) of this alternative micro-sampling device where it remains so threaded throughout the procedure. (If a small air bubble is observed at this end of the capillary, action may be taken as described above to plug the other end further to eliminate such a bubble).

The sample obtained thus runs down onto the platform (10) where it collects. The device comprising the platform (10), the probe (9) over which the capillary tube (8) is threaded and support rod (11) is then lowered into the vessel or cuvette (12). The sample is then stirred in by gentle movement so that all of the sample is washed from the platform and mixed into the diluent.

The other sample capillary tube is then treated in a similar way and results may be obtained as described above.

A device similar to that shown in FIG. 2 used in basically a similar manner, but having an additional probe or probes, allows diluent and/or reagent or reagents to be measured for mixing with the sample and avoids the need to make any volumetric measurements.

The following Examples serve to illustrate the invention.

A number of different types of micro-sampling devices have been made, and tested, all of which use the same basic method of displacement of the specimen by a probe, and the subsequent washing of the displaced sample by a measured diluent. The following tests and results are considered to be valid for all types of device operating in accordance with this invention.

EXAMPLE 1 (REPRODUCIBILITY)

Ten specimen capillaries were filled with horse serum, to which a suitable amount of $I^{125}$ was added, the ends plugged with modelling clay and specimens were sampled as previously described. An uncalibrated micro-sampler of approximately 20 $\mu l$ was used. A diluent of only 0.1 ml of water was used to wash the sample into the counting vessel, thus testing the reproducibility resulting from minimal diluent. The time in seconds for a total count of 10,000 was recorded.

| Sample | Seconds | | |
|---|---|---|---|
| 1 | 253 | | |
| 2 | 258 | | |
| 3 | 252 | Mean | 259.2 |
| 4 | 265 | Variance | 28.78 |
| 5 | 262 | Standard | 5.3644 |
| 6 | 256 | Deviation S.D. | |
| 7 | 266 | | |
| 8 | 264 | | |
| 9 | 264 | | |
| 10 | 252 | | |

EXAMPLE 2 (REPRODUCIBILITY)

A similar test was made to compare the reproducibility of the results of using a micro-sampling device of the invention with those of using a traditional micro pipette technique. The best eight of the ten results for each are shown, because air bubbles were noted in the diluent dispensing system of the micro-sampling device in the first and second sampling operations of the micro-sampling device.

| | Micro Sampling Device | | |
|---|---|---|---|
| Sample | Seconds | | |
| 3 | 278 | | |
| 4 | 281 | Mean | 277.7 |
| 5 | 282 | Variance | 13.09 |
| 6 | 278 | S.D. | 3.611 |
| 7 | 273 | | |
| 8 | 277 | | |
| 9 | 271 | | |
| 10 | 275 | | |

| | Traditional Technique | | |
|---|---|---|---|
| Sample | Seconds | | |
| 2 | 320 | | |
| 3 | 326 | Mean | 320.25 |
| 4 | 317 | Variance | 12.187 |
| 5 | 323 | S.D. | 3.491 |
| 7 | 321 | | |
| 8 | 319 | | |
| 9 | 314 | | |
| 10 | 322 | | |

Examples 1 and 2 thus illustrate the reproducibility of results when using the micro-sampling device according to the invention which, as shown by Example 2, compare favourably with those using a traditional micro pipette technique.

EXAMPLE 3 (ANALYTICAL TESTS)

A small number of analytical measurements have been performed on samples obtained during clinical studies. The following is a comparison of results of blood glucose determinations, using samples taken with the micro-sampling device of this invention and routine samples taken using an Eppendorf syringe. The values are in $mM/cm^3$.

| Specimen | Micro-Sampling Device | Routine Samples |
|---|---|---|
| 1 | 12.5 | 8.0 |
| 2 | 18.5 | 14.0 |
| 3 | 5.75 | 4.4 |
| 4 | — | — |
| 5 | 12.0 | 11.4 |
| 6 | 7.5 | 6.8 |
| 7 | 14.5 | 13.4 |
| 8 | 13.0 | 12.4 |
| 9 | 7.0 | 6.1 |
| 10 | 25.0 | 22.1 |
| Coefficiet of correlation | 0.9665 | |
| Slope | 0.8593 | |
| Intercept | 0.0963 | |

EXAMPLE 4 (ANALYTICAL TESTS)

Three measurements of serum albumin performed on healthy individuals, using the micro-sampling system were:

(Normal range 30 to 50 gms/liter)
1. 41 gms/liter
2. 42 gms/liter
3. 43 gms/liter One measurement only (3) was performed in duplicate. Agreement was within ±0.5%.

From these results, it can be seem that the micro-sampling device of this invention provides a micro-sampling device which offers an alternative to traditional techniques, but demands less skill. In other applications where the taking of a small specimen volume for subsequent analysis is desirable (e.g. paediatric practice, general practice) and when only one analysis per specimen is required, this device could also be of value.

I claim:

1. A micro-sampling device for accurately measuring a desired volume of a micro-sample of a fluid, comprising:
   (1) specimen container means for containing a specimen of said fluid to be sampled, said specimen container means having a capillary bore extending longitudinally thereof and having an open end through which said fluid is received into said capillary bore by capillary action;
   (2) support means; and
   (3) solid probe means angularly disposed on said support means for accurately displacing a desired measured volume of said fluid from said specimen container means upon threadedly placing said capillary bore open end onto said probe means, said support means being selectively positionable in relation to a separate collection means;
   whereby the extent to which said capillary bore open end is placed onto said probe means controls the volume of fluid displaced from the capillary bore to give said desired measured volume of fluid.

2. A device according to claim 1, wherein said solid probe means is provided in the form of a probe unit comprising:
   (a) a probe support member having two planar portions connected to one another substantially at right angles; and
   (b) a solid probe attached at an acute angle to one of said planar portions and having its free end extending in a direction toward said other planar portion, said one planar portion to which said solid probe is attached terminating in a vertex, said free end of said solid probe being positioned in relation to said other planar portion such that said capillary bore open end is threadedly placeable onto said solid probe to displace said desired volume of fluid from said capillary bore.

3. A device according to claim 2, and further comprising means defining a hole in said other planar portion adjacent to the angle between said two planar portions.

4. A probe unit substantially as defined in claim 2.

5. A device according to claim 1, wherein said solid probe means is provided in the form of a probe unit comprising:
   (a) a solid probe; and
   (b) a platform means for supporting said solid probe having a platform face, said desired volume of fluid displaced from said capillary bore being receiveable by said platform means when said capillary bore open end is threadedly placed onto said solid probe so that said capillary bore open end contacts said platform face.

6. A device according to claim 5, wherein said platform means includes a dished surface for receiving said displaced fluid.

7. A probe unit substantially as defined in claim 5.

8. A micro-sampling device for accurately measuring a desired volume of a micro-sample of fluid, comprising:
   (1) specimen container means for containing a specimen of said fluid to be sampled, said specimen container means having a capillary bore extending longitudinally thereof and having an open end through which said fluid is received into said capillary bore by capillary action;
   (2) support means;
   (3) solid probe means mounted on said support means for accurately displacing a desired measured volume of said fluid from said specimen container means upon insertion of said probe means into said capillary bore open end, said support means being selectively positionable in relation to a separate collection means;
   (4) probe indexing means associated with said solid probe means for selectively indexing the extent to which said solid probe means is inserted into said capillary bore, thereby to control the volume of fluid displaced from said capillary bore to give said desired measured volume of fluid.

9. A device according to claim 8, wherein said solid probe indexing means includes at least one index point and means selectively engageable with said at least one index point to control the extent of insertion of said solid 10. A process for analyzing a microsample of a fluid, comprising:
   (a) providing a specimen container means for containing a specimen of said fluid to be analyzed, said specimen container means having a capillary bore extending longitudinally thereof and having an open end through which said fluid is received into said capillary bore by capillary action;
   (b) causing said fluid to be analyzed to enter said capillary bore through said open end;
   (c) providing a solid probe means angularly disposed on a support means for accurately displacing a desired predetermined volume of a micro-sample of said fluid from said container means;
   (d) displacing an accurate predetermined volume of a micro-sample of said fluid from said capillary bore by controlled penetration of said solid probe means into said capillary bore;
   (e) collecting the fluid displaced upon said penetration; and
   (f) analyzing said collected displaced fluid.

* * * * *